United States Patent [19]

Nakamura et al.

[11] Patent Number: 5,071,994
[45] Date of Patent: Dec. 10, 1991

[54] 2-ARYL-4-HALOMETHYL-4-ISOXAZOLIN-3-ONE DERIVATIVES

[75] Inventors: Koki Nakamura; Shigeru Nakamura, both of Kanagawa, Japan

[73] Assignee: Fuji Photo Film Co., Ltd., Kanagawa, Japan

[21] Appl. No.: 644,858

[22] Filed: Jan. 23, 1991

Related U.S. Application Data

[63] Continuation of Ser. No. 152,719, Feb. 5, 1988, abandoned.

[30] Foreign Application Priority Data

Feb. 5, 1987 [JP] Japan .................................. 62-25443

[51] Int. Cl.$^5$ .................... C07D 261/12; A61K 31/42
[52] U.S. Cl. .................................... 548/243; 430/380; 514/380
[58] Field of Search ........................................ 548/243

[56] References Cited

U.S. PATENT DOCUMENTS

| | | |
|---|---|---|
| 3,119,832 | 1/1964 | Matter et al. .......... 548/243 |
| 4,490,462 | 12/1984 | Kawaguchi et al. ........ 430/543 |
| 4,783,396 | 11/1988 | Nakamura et al. ........ 430/353 |
| 4,886,736 | 12/1989 | Nakamura et al. ........ 430/958 |
| 4,950,764 | 8/1990 | Nakamura et al. ........ 548/243 |

FOREIGN PATENT DOCUMENTS 104274  8/1980  Japan .

OTHER PUBLICATIONS

*Organic Chemical Nomenclature* by Phillip Fresenius (Halsted Press), p. 27 (1989).
Nakamura et al., Chemical Abstracts, vol. 109, No. 83227 (1988) (Abstract for JP 293243, 12/19/87).
Hirai et al., Chemical Abstracts, vol. 109, No. 83528 (1988) (Abstract for JP 244044, 10/24/87).
Nakamura et al., Chemical Abstracts, vol. 109, No. 180480 (1980) (Abstract for JP 180480, 10/26/87).

*Primary Examiner*—Mukund J. Shah
*Assistant Examiner*—F. Bernhardt
*Attorney, Agent, or Firm*—Sughrue, Mion, Zinn, Macpeak & Seas

[57] ABSTRACT 2-aryl-4-halomethyl-4-isoxazolin-3-1-derivatives of formula (I), useful as intermediates for positive working compounds in silver halide photographic materials

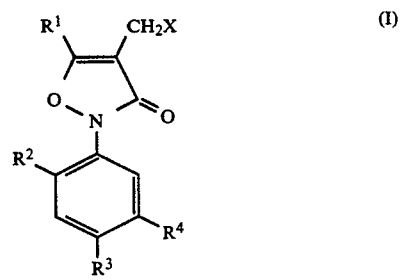

wherein $R^1$ represents a substituted or unsubstituted alkyl having from 1 to 6 carbon atoms or a substituted or unsubstituted aryl having from 6 to 24 carbon atoms; $R^2$, $R^3$, and $R^4$, are the same or different, each having up to 20 carbon atoms and each represents hydrogen, a substituted or unsubstituted alkoxy, a substituted or unsubstituted aryloxy, a substituted or unsubstituted acyl, a substituted or unsubstituted alkoxycarbonyl, a substituted or unsubstituted aryloxycarbonyl, halogen, nitro, a substituted or unsubstituted carbamoyl, a substituted or unsubstituted sulfamoyl, a substituted or unsubstituted sulfonyl, cyano, trifluoromethyl, or carboxyl, with the proviso that at least one of said $R^2$ and $R^3$ is cyano, a substituted or unsubstituted sulfonyl, trifluoromethyl, or nitro, and X represents fluorine, chlorine, bromine or iodine.

5 Claims, No Drawings

2-ARYL-4-HALOMETHYL-4-ISOXAZOLIN-3-ONE DERIVATIVES

This is a continuation of application Ser. No. 07/152,719, filed Feb. 5, 1988 now abandoned.

FIELD OF THE INVENTION

This invention relates to 2-aryl-4-halomethyl-4-isoxazolin-3-one derivatives, and more particularly to 2-aryl-4-halomethyl-4-isoxazolin-3-one derivatives useful as intermediates for positive working compounds in silver halide photographic materials. Further, these derivatives are also useful as physiologically active materials.

BACKGROUND OF THE INVENTION

Various 2-arylisoxazolin-3-one derivatives and synthesis methods thereof are described in *Heterocycles*, 20(6), pages 1123–1126 (1983), *Chemical and Pharmaceutical Bulletin*, 30(9), pages 3097–3105, *Heterocycles*, 19(3), pages 515–520, *Heterocycles*, 19(3), pages 521–524, *Journal of Heterocyclic Chemistry*, 17(4), pages 727–731, *Chemical and Pharmaceutical Bulletin*, 19(7), pages 1389–1394, Japanese Patent Application (OPI) No. 104274/80 (the term "OPI" as used herein means an "unexamined published application"), etc.

However, 2-arylisoxazolin-3-one derivatives wherein the substituent at the 2-position of the isoxazoline nucleus is an aryl group substituted by an electron attractive group(s) having a higher electron attractive property than a chlorine group have never been known and also such derivatives having a halomethyl group at the 4-position of the isoxazoline nucleus have never been known.

SUMMARY OF THE INVENTION

An object of this invention is, therefore, to provide a 2-aryl-4-halomethyl-4-isoxazolin-3-one derivative wherein the isoxazoline nucleus is substituted by a halomethyl group at the 4-position thereof and is substituted by an aryl group at the 2-position thereof, the aryl group containing an electron attractive group(s) having a higher electron attractive property than a chlorine group.

That is, the invention is concerned with a 2-aryl-4-halomethyl-4-isoxazolin-3-one derivative represented by formula (I)

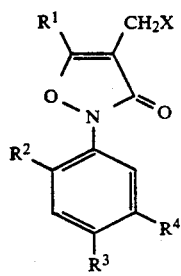

wherein $R^1$ represents an alkyl group which may be substituted or an aryl group which may be substituted; $R^2$, $R^3$, and $R^4$, which may be the same or different, each represents a hydrogen atom, an alkoxy group which may be substituted, an aryloxy group which may be substituted, an acyl group which may be substituted, an alkoxycarbonyl group which may be substituted, an aryloxycarbonyl group which may be substituted, a halogen atom, a nitro group, a carbamoyl group which may be substituted, a sulfamoyl group which may be substituted, a sulfonyl group which may be substituted, a cyano group, a trifluoromethyl group, or a carboxyl group, with the proviso that at least one of $R^2$ and $R^3$ is a cyano group, a sulfonyl group which may be substituted, a trifluoromethyl group, or a nitro group; and X represents a halogen atom.

DETAILED DESCRIPTION OF THE INVENTION

In formula (I) described above, $R^1$ is an alkyl group which may be substituted (e.g., a methyl group, an ethyl group, an isopropyl group, a cyclohexyl group, a t-butyl group, a chloromethyl group, an N-methylacetylaminomethyl group, an octylthiomethyl group, an adamantyl group, an undecyl group, a heptadecyl group, etc.) or an aryl group which may be substituted (e.g., a phenyl group, a 2-methylphenyl group, a 4-methylphenyl group, a 4-methoxyphenyl group, a 3-methoxy-4-acetamidophenyl group, a 4-dodecyloxyphenyl group, a 4-octadecyloxyphenyl group, a 3-sulfo-4-methoxyphenyl group, etc.).

The alkyl group shown by $R^1$ preferably has from 1 to 6 carbon atoms and the aryl group shown by $R^1$ preferably has from 6 to 24 carbon atoms. Particularly preferred examples of $R^1$ are a methyl group, a t-butyl group, a phenyl group, an alkoxy-substituted phenyl group.

$R^2$, $R^3$, and $R^4$ in formula (I) each is a hydrogen atom, an alkoxy group or aryloxy group, either of which may be substituted (e.g., a methoxy group, a 2-methoxyethoxy group, a phenoxy group, a 4-n-hexadecylcarbamoylphenoxy group, an ethoxy group, a n-hexyloxy group, a n-hexadecyloxy group, a methoxypropyl group, etc.), an acyl group which may be substituted (e.g., an acetyl group, a n-dodecanoyl group, a benzoyl group, a 2-ethoxycarbonylbenzoyl group, a 2,2-dimethylpropanoyl group, etc.), an alkoxycarbonyl group or aryloxycarbonyl group, either of which may be substituted (e.g., a methoxycarbonyl group, an ethoxycarbonyl group, a n-octyloxycarbonyl group, a n-hexadecyloxycarbonyl group, a phenoxycarbonyl group, etc.), a sulfonyl group which may be substituted (e.g., a methylsulfonyl group, a chloromethylsulfonyl group, an ethylsulfonyl group, a n-dodecylsulfonyl group, a n-tetradecylsulfonyl group, a phenylsulfonyl group, a 4-methylphenylsulfonyl group, a t-dodecylsulfonyl group, etc.), a carbamoyl group which may be substituted (e.g., a carbamoyl group, a dimethylcarbamoyl group, a diethylcarbamoyl group, a n-butylcarbamoyl group, a 3-(2,4-di-t-pentylphenoxy)propylcarbamoyl group, an N-methyl-N-n-octylbarbamoyl group, a (3-hexadecylsulfamoyl)phenylcarbamoyl group, an N-methyl-N-n-octadecylcarbamoyl group, a n-hexadecylcarbamoyl group, a 3-n-dodecyloxypropylcarbamoyl group, etc.), a sulfamoyl group which may be substituted (e.g., a methylsulfamoyl group, a dimethylsulfamoyl group, a diethylsulfamoyl group, a dibutylsulfamoyl group, an N-methyl-N-n-hexylsulfamoyl group, an N-methyl-N-n-octylsulfamoyl group, an N-methyl-N-n-hexadecylsulfamoyl group, an N-methyl-N-n-octadecylsulfamoyl group, a n-dodecylsulfamoyl group, an N-phenyl-N-hexadecylsulfamoyl group, an N-methyl-N-3-methoxypropylsulfamoyl group, a bis(2-methoxyethyl)sulfamoyl group, etc.), a nitro group, a cyano group, a halogen atom, a carboxyl group, or a trifluoromethyl group, with the proviso that at least one of $R^2$ and $R^3$ is a nitro group, a cyano group, a sulfonyl group which may be substitited, or a trifluoromethyl group.

It is preferred that at least one of $R^2$ and $R^3$ is a nitro group or a sulfonyl group, and it is particularly preferred that at least one of $R^2$ and $R^3$ is a nitro group.

Also, the compound of formula (I) wherein one of $R^2$ and $R^3$ is a nitro group and the other of $R^2$ and $R^3$ and/or $R^4$ is a sulfonyl group, a sulfamoyl group, an alkoxycarbonyl group, a carbamoyl group, an acyl group, a trifluoromethyl group, or a cyano group is preferred.

In particular, the compound of formula (I) wherein $R^2$ is a nitro group, $R^3$ is a sulfamoyl group, a carbamoyl group, an alkoxycarbonyl group, or a trifluoromethyl group, and $R^4$ is a hydrogen atom is preferred.

X represents a halogen atom (e.g., a fluorine atom, a chloride atom, a bromine atom, or an iodine atom).

Specific examples of the compound of this invention shown by formula (I) are illustrated below, but the invention is not limited to these compounds:

| Compound | Melting point (°C.) |
|---|---|
| (1) [structure with t-C$_4$H$_9$, CH$_2$Cl, O$_2$N, OC$_{16}$H$_{33}$, COOC$_2$H$_5$] | oily material |
| (2) [structure with t-C$_4$H$_9$, CH$_2$Cl, O$_2$N, CON(CH$_3$)(C$_{18}$H$_{37}$)] | 77 |
| (3) [structure with t-C$_4$H$_9$, CH$_2$Cl, O$_2$N, SO$_2$N(CH$_3$)$_2$] | 163~164 |
| (4) [structure with t-C$_4$H$_9$, CH$_2$Cl, O$_2$N, CONHC$_{16}$H$_{33}$] | 48 |
| (5) [structure with t-C$_4$H$_9$, CH$_2$Cl, O$_2$N, SO$_2$N-morpholino] | 165~166 |
| (6) [structure with t-C$_4$H$_9$, CH$_2$Cl, O$_2$N, SO$_2$N(CH$_3$)(C$_{18}$H$_{37}$)] | 55~56 |
| (7) [structure with t-C$_4$H$_9$, CH$_2$Cl, O$_2$N, SO$_2$N(C$_2$H$_5$)$_2$] | 118~119 |
| (8) [structure with t-C$_4$H$_9$, CH$_2$Cl, O$_2$N, SO$_2$N(CH$_3$)(C$_{16}$H$_{33}$)] | 56 |

-continued
| Compound | Melting point (°C.) |
|---|---|
| (9) 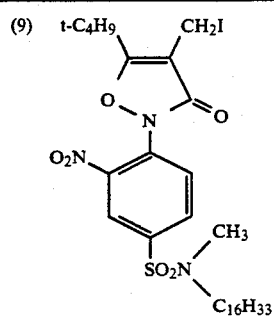 | 56~57 |
| (10) 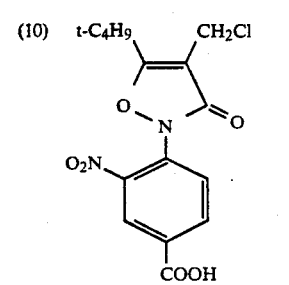 | 217 (decompd.) |
| (11) 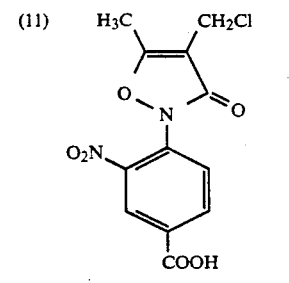 | 190~191 (decompd.) |
| (12) 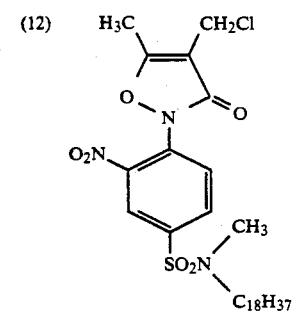 | 59~61 |
| (13) 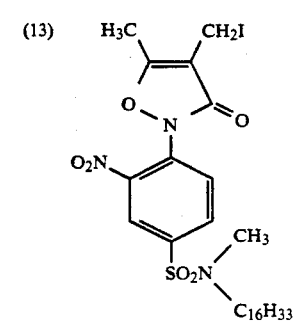 | 70~71 |
-continued
| Compound | Melting point (°C.) |
|---|---|
| (14) 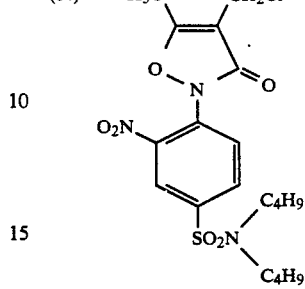 | 57~58 |
| (15) 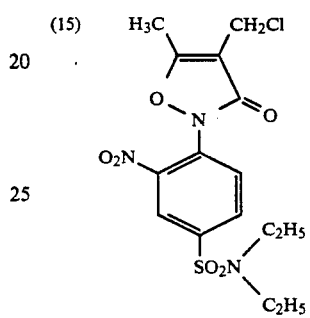 | 138 |
| (16) 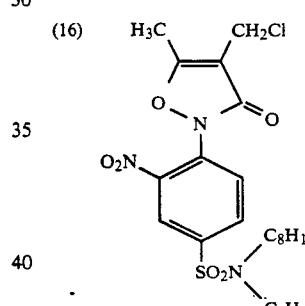 | 79~80 |
| (17) 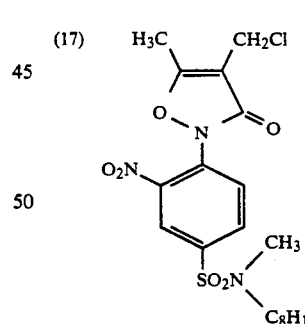 | 63~64 |
| (18) 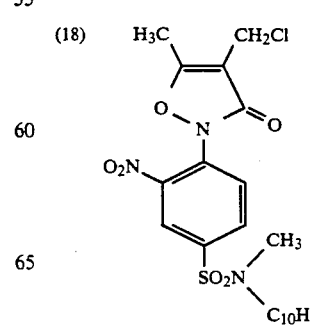 | 41~42 |

-continued

| Compound | Melting point (°C.) |
|---|---|
| (19) [structure: 5-t-C4H9, 4-CH2Cl isoxazolone; N-aryl with 2-C14H29SO2 and 4-SO2CH3] | 110~111 |
| (20) [structure: 5-t-C4H9, 4-CH2Cl isoxazolone; N-aryl with 2-SO2N(CH3)(C18H37) and 4-NO2] | 48~50 |
| (21) [structure: 5-t-C4H9, 4-CH2F isoxazolone; N-aryl with 2-NO2 and 4-SO2N(CH3)(C16H33)] | 55~56 |
| (22) [structure: 5-CH3, 4-CH2Cl isoxazolone; N-aryl with 2-NO2 and 4-CONHCH2CH2CH2OC12H25] | 66~67 |
| (23) [structure: 5-CH3, 4-CH2Cl isoxazolone; N-aryl with 2-NO2 and 4-CF3] | 68~70 |
| (24) [structure: 5-n-C11H23, 4-CH2Cl isoxazolone; N-aryl with 2-CH3SO2, 4-CF3, 5-SO2CH3] | 110~111 |
| (25) [structure: 5-(4-C16H33O-phenyl), 4-CH2Cl isoxazolone; N-aryl with 2-NO2 and 4-SO2N(CH3)2] | 133~135 |
| (26) [structure: 5-(4-CH3O-3-CH2Cl-phenyl), 4-CH2Cl isoxazolone; N-aryl with 2-NO2 and 4-SO2N(C2H5)2] | 136~137 |
| (27) [structure: 5-phenyl, 4-CH2Cl isoxazolone; N-aryl with 2-NO2 and 4-SO2N(CH3)(C18H37)] | 94~95 |

| Compound | Melting point (°C.) |
|---|---|
| (28) 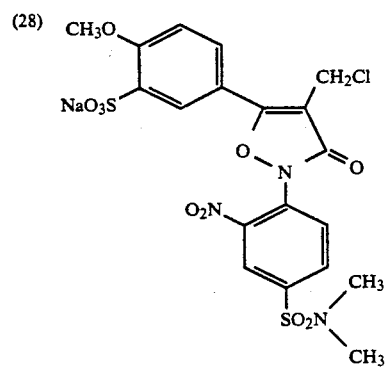 | >260 |
| (29) 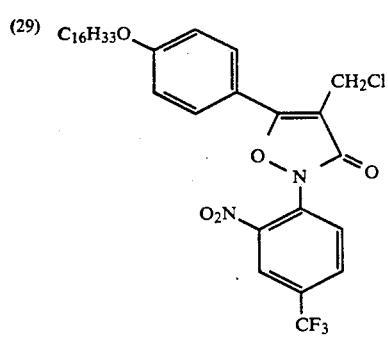 | 64~65 |
| (30) 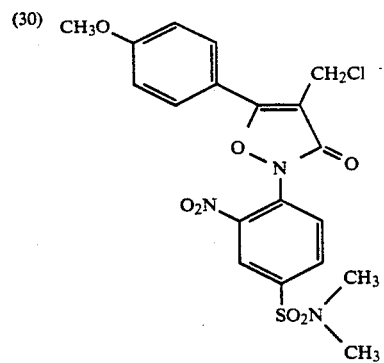 | 156~157 |
| (31) 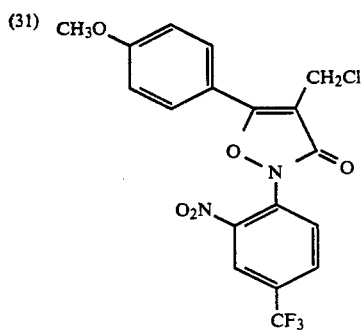 | 135~136 |
| Compound | Melting point (°C.) |
|---|---|
| (32) 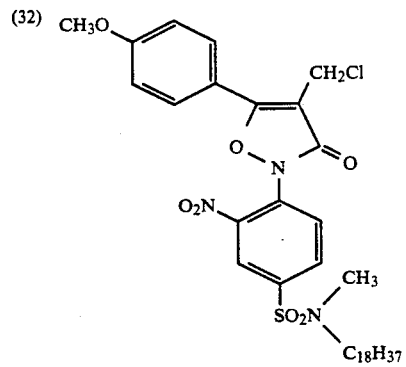 | 77~79 |
| (33) 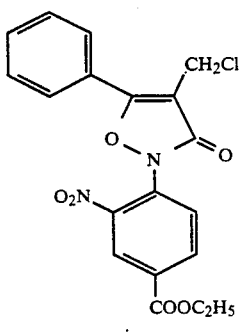 | 190~191 |
| (34) 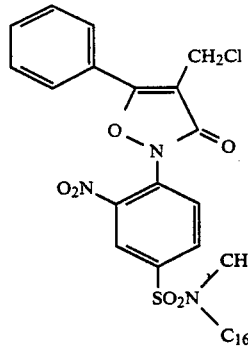 | 95~97 |
| (35) 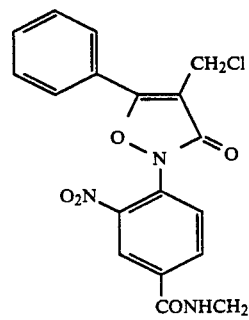 | 110~111 |

| Compound | | Melting point (°C.) |
|---|---|---|
| (36) 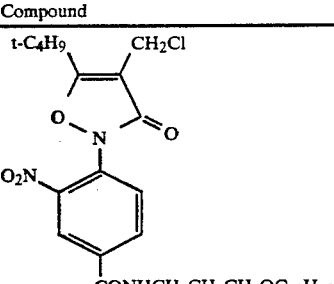 | | oily material |
| (37) 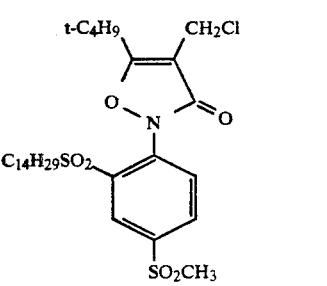 | | 110~111 |

A 2-aryl-4-isoxazolin-3-one derivative which is used as a raw material for producing the compound of this invention shown by formula (I) described above can be generally synthesized by following method (A) or (B).

METHOD (A)

A method of obtaining the 4-isoxazolin-3-one derivative by N-acylating a nitrogen-substituted hydroxylamine with a propionic acid derivative (ester or acid halide) and ring-closing this N-acylated product under basic conditions (examples of this method are described in *Chemical Abstracts*, Vol. 76, No. 23, 140775a, ibid., Vol. 75, No. 17, 110227k, etc.) or a method of obtaining the 4-isoxazolin-3-one derivative by N-acylating a nitrogen-substituted hydroxylamine with a diketene or a β-keto-acid derivative and performing the dehydration ring-closure of the N-acylated product (examples of this method are described in *Heterocycles*, Vol. 20, No. 6, pages 1123–1126, ibid., Vol. 19, No. 3, pages 521–524, etc.).

METHOD (B)

A method of obtaining the 4-isoxazolin-3-one derivative by performing the displacement reaction of an aromatic compound active to an aromatic nucleophilic displacement, such as a benzene having an electron attractive group at the 2-position or conjugated position thereof and 3-hydroxyisoxazole in an aprotic polar solvent such as dimethyl sulfoxide or dimethylformamide under basic conditions.

Also, to synthesize the compound of this invention shown by formula (I) from the 2-aryl-4-isoxazolin-3-one derivative produced by the aforesaid methods, the following method can be employed.

That is, the compound of this invention can be obtained by heating the 2-aryl-4-isoxazolin-3-one derivative, an excessive amount (usually about 3 to 20 equivalents) of paraformaldehyde, and about 1 to 2 equivalents of anhydrous zinc chloride in a solvent such as a halogen-series solvent (e.g., methylene chloride, chloroform, 1,2-dichloroethane, etc.) or acetic acid while blowing hydrogen chloride gas into the reaction system.

The compounds of this invention shown by formula (I) described above are important intermediates for synthesizing a group of particularly important compounds known as positive working compounds capable of releasing photographically useful reagents by causing an oxidation-reduction reaction.

The positive working compounds prepared using the compounds of this invention as intermediate compounds have various advantages as described, for example, in Japanese Patent Application (OPI) Nos. 244044/87 and 245256/87 and U.S. application Ser. Nos. 925,350 (filed Oct. 30, 1986) now U.S. Pat. No. 4,783,396 and 65,194 (filed June 12, 1987).

Also, the compounds of this invention have herbicidal activity and pharmacological activities as sterilizers, analgesic agents, anti-inflammatory agents, etc., and thus are important as physiologically active materials.

Then, the invention is further explained more practically by the following examples.

EXAMPLE 1

Synthesis of Compound (2)

Synthesis Example 1-1

Synthesis of N-methyl-N-octadecyl-3-nitro-4-chlorobenzamide

After adding 68.6 g of thionyl chloride to a mixture of 105.7 g of 3-nitro-4-chlorobenzoic acid and 800 ml of acetonitrile, the resultant mixture was refluxed for 4 hours. After cooling the reaction mixture, the solvent was distilled off and the residue formed was dissolved in chloroform. To the solution formed was added 63.5 g of triethylamine and after adjusting the temperature thereof to 5° C., a chloroform solution of 148.6 g of N-methyloctadecylamine was added dropwise to the solution. After the reaction was over, water was added to the reaction mixture and the organic phase thus formed was recovered and dried over anhydrous sodium sulfate. After removing inorganic matters by filtration from the organic phase, the solvent was distilled from the organic phase and the residue was recrystallized from a 1:3 mixture of acetonitrile and methanol to provide 186 g of the above-described compound with a yield of 76.0%. The melting point thereof was 55° C. to 56° C.

Synthesis Example 1-2

Synthesis of 5-t-butyl-2-(4-N-methyl-N-octadecylcarbamoyl-2-nitrophenyl)-4-isoxazolin-3-one After adding 300 ml of dimethylformamide to a mixture of 34.1 g of N-methyl-N-octadecyl-3-nitro-4-chlorobenzamide prepared in the above step, 12.4 g of 5-t-butyl-3-hydroxyisoxazole, and 12.4 g of potassium carbonate, the reaction was performed for 5 hours at 100° C. After the reaction was over, the solvent was distilled off under reduced pressure from the reaction mixture and ethyl acetate and water were added to the residue formed followed by stirring. The organic phase thus formed was recovered, applied to silica gel column chromatography, and the main product thus obtained was recrystallized from a mixture of n-hexane and ethyl acetate to provide 18.0 g of of the above-described compound with a yield of 43.1%. The melting point thereof was 64° C.

Synthesis Example 1-3

Synthesis of Compound (2), 4-chloromethyl-5-t-butyl-2-(4-N-methyl-N-octadecyl-carbamoyl-2-nitrophenyl)-4-isoxazolin-3-one After mixing 36 g of 5-t-butyl-2-(4-N-methyl-N-octadecylcarbamoyl-2-nitrophenyl)-4-isoxazolin-3-one prepared in the above step, 5.7 g of paraformaldehyde, 10.3 g of zinc chloride, and 250 ml of acetic acid, the reaction was performed for 20 hours at 100° C. while blowing hydrogen chloride gas into the reaction system. After the reaction was over, the reaction mixture was cooled and poured into ice-water. Solids thus deposited were recovered by filtration, dissolved in chloroform, and purified by column chromatography to provide 10.0 g of the desired compound with a yield of 25.6%. The melting point thereof was 77° C.

| Elemental Analysis: | C (%) | H (%) | N (%) |
|---|---|---|---|
| Calcd. | 65.84 | 8.78 | 6.77 |
| Found | 66.01 | 8.72 | 6.70 |

EXAMPLE 2

Synthesis of Compound (3)

Synthesis Example 2-1

Synthesis of 5-t-butyl-2-(4-dimethylsulfamoyl-2-nitrophenyl)-4-isoxazolin-3-one In 100 ml of dimethyl sulfoxide were dissolved 26.5 g of dimethyl 4-chloro-3-nitrobenzenesulfonamide and 17.0 g of 5-t-butyl-3-hydroxyisoxazole and after adding thereto 17 g of potassium carbonate, the reaction was performed for 7 hours at 65° C. After the reaction was over, the reaction mixture obtained was poured into cold diluted hydrochloric acid followed by stirring to deposit crystals which were then recovered by filtration and recrystallized from methanol to provide 33.1 g of the above-described compound with a yield of 89.5%. The melting point thereof was 167° C. to 168° C.

Synthesis Example 2-2

Synthesis of Compound (3), 5-t-butyl-4-chloromethyl-2-(4-dimethyl-sulfamoyl-2-nitrophenyl)-4-isoxazolin-3-one After mixing 11.8 g of 5-t-butyl-2-(4-dimethylsulfamoyl-2-nitrophenyl)-4-isoxazolin-3-one prepared in the above step, 50 ml of acetic acid, 4.3 g of paraformaldehyde, and 6.5 g of zinc chloride, the mixture obtained was refluxed for 5.5 hours while blowing hydrogen chloride gas into the reaction system. After the reaction was over, the solvent was distilled off from the reaction mixture under reduced pressure and the residue was extracted with water and ethyl acetate. The organic phase thus obtained was washed twice with an aqueous solution of sodium bicarbonate and the solvent was distilled off from the organic phase. The oily product thus formed was applied to silica gel column chromatography to provide 5.4 g of the above-described compound as the main product with a yield of 40.4%. The melting point thereof was 163° C. to 164° C.

| Elemental Analysis: | C (%) | H (%) | N (%) |
|---|---|---|---|
| Calcd. | 45.99 | 4.82 | 10.06 |
| Found | 45.73 | 4.80 | 10.00 |

EXAMPLE 3

Synthesis of Compound (7)

Synthesis Example 3-1

Synthesis of 5-t-butyl-2-(4-diethylsulfamoyl-2-nitrophenyl)-4-isoxazolin-3-one After mixing 35 g (0.42) of diethyl 4-chloro-3-nitrobenzenesulfonamide, 120 ml of dimethyl sulfoxide, 20 g of 5-t-butyl-3-hydroxyisoxazole, and 20 g of potassium carbonate, the reaction was performed for 3 hours at 60° C. After the reaction was over, the reaction mixture was cooled and poured into water. Crystals thus formed were recovered by filtration, washed with water, dried, and then recrystallized from a mixture of methanol and water to provide 41.0 g (0.103) of the above-described compound with a yield of 92.1%. The melting point thereof was 87° C. to 88° C.

Synthesis Example 3-2

Synthesis of Compound (7), 5-t-butyl-4-chloromethyl-2-(4-diethyl-sulfamoyl-2-nitrophenyl)-4-isoxazolin-3-one After mixing 49 g (0.101) of 5-t-butyl-2-(4-diethylsulfamoyl-2-nitrophenyl)-4-isoxazolin-3-one prepared in the above step, 150 ml of acetic acid, 14 g of paraformaldehyde, 16.5 g of zinc chloride, and 5 ml of sulfuric acid, the mixture was refluxed for 8 hours while blowing hydrogen chloride gas into the system. After the reaction was over, the reaction mixture obtained was cooled and poured into water. Crystals thus deposited were recovered by filtration, washed with water, and dried to provide 36.3 g of the desired product with a yield of 80.6%. The melting point thereof was 118° C. to 119° C.

| Elemental Analysis: | C (%) | H (%) | N (%) |
|---|---|---|---|
| Calcd. | 48.48 | 5.42 | 9.42 |
| Found | 48.48 | 5.44 | 9.39 |

EXAMPLE 4

Synthesis of Compound (8)

Synthesis Example 4-1

Synthesis of 5-t-butyl-3-hydroxyisoxazole

In 2 liters of an aqueous 4N sodium hydroxide solution was dissolved 583.7 g of hydroxylamine hydrochloride, 2 liters of ethanol was added to the solution under ice-cooling, and after further adding a 1:1 mixture of an aqueous 4N sodium hydroxide solution and ethanol to the mixture, the pH of the mixture was adjusted to 10.0. Also, 1380 g of ethyl pivaloylacetate and a 1:1 mixture of an aqueous 4N sodium hydroxide solution and ethanol were simultaneously added dropwise to the mixture so that the pH thereof became 10±0.2 and the temperature became 0° to 5° C.

Thereafter, the resultant mixture was stirred for 2 hours at room temperature and poured into 6 kg of concentrated hydrochloric acid at 0° C., and the mixture was allowed to stand for 12 hours. Crystals thus deposited were recovered by filtration, washed well with water, and dried to provide 770 g of the above-described compound with a yield of 68.2%. The melting point thereof was 99° C. to 101° C.

Synthesis Example 4-2

Synthesis of 4-chloro-3-nitrobenzenesulfonyl chloride

To a mixture of 1280 g of potassium 4-chloro-3-nitrobenzenesulfonate, 1150 ml of acetonitrile, 250 ml of sulforan, and 30 ml of dimethylacetamide was added dropwise 1250 ml of phosphorus oxychloride so that the internal temperature was kept at 60° C. to 70° C. Then, after performing the reaction for 3 hours at 73° C., the reaction mixture was cooled with water and after adding slowly 400 ml of water thereto, the mixture was poured into 5 liters of ice-water. Crystals thus deposited were recovered by filtration, washed, and dried to provide 1060 g of the above-described compound with a yield of 84%. The melting point thereof was 55° C. to 56° C.

Synthesis Example 4-3

Synthesis of 4-chloro-3-nitro-N-hexadecylbenzenesulfonamide

To one liter of dichloromethane was added 800 g of 4-chloro-3-nitrobenzenesulfonyl chloride prepared in the above step and the mixture was cooled to 0° C. Then, a mixture of 600 g of hexadecylamine, 251 ml of triethylamine, and 780 ml of dichloroethane was added dropwise to the mixture at 20° C. to 30° C. After performing the reaction for 2 hours at room temperature, the dichloromethane was distilled off from the reaction mixture under reduced pressure and the residue was dissolved in 3 liters of methanol under heating. After gradually cooling the solution to room temperature to form crystals, 3 liters of methanol was added to the solution and the mixture was ice-cooled to deposit crystals which were then recovered by filtration and dried to provide 1020 g of the above-described compound with a yield of 88%. The melting point thereof was 91° C. to 93° C.

Synthesis Example 4-4

Synthesis of 4-chloro-3-nitro-N-methyl-N-hexadecylbenzenesulfonamide

In 640 ml of acetone was dissolved 170 g of 4-chloro-3-nitro-N-hexadecylbenzenesulfonamide prepared in the above step and after adding thereto 79 g of potassium carbonate, 6 ml of polyethylene glycol (average molecular weight: 400), and 71 g of dimethylsulfuric acid, the mixture was refluxed for 5 hours. To the reaction mixture thus obtained was added 240 ml of acetone and after adding dropwise 870 ml or water to the mixture at 40° C., the resultant mixture was cooled to room temperature, whereby crystals deposited. The crystals were recovered by filtration, washed with water and then methanol, and dried to provide 169 g of the above-described compound with a yield of 97%. The melting point thereof was 74° C. to 75° C.

Synthesis Example 4-5

Synthesis of 5-t-butyl-2-(4-N-methyl-N-hexadecylsulfamoyl-2-nitrophenyl)-4-isoxazolin-3-one After mixing 470 g of 4-chloro-3-nitro-N-methyl-N-hexadecylbenzenesulfonamide prepared in Synthesis Example 4-4, 169 g of 5-t-butyl-3-hydroxyisoxazole prepared in Synthesis Example 4-1, 168 g of potassium carbonate, and 1.2 liters of dimethyl sulfoxide, the reaction was performed for 6 hours at 65° C. After the reaction was over, the reaction mixture formed was poured into ice-water and crystals thus deposited were recovered by filtration and dried to provide 576 g of the aforesaid compound with a yield of 100%. The melting point thereof was 67° C. to 68° C.

Synthesis Example 4-6

Synthesis of Compound (8), 5-t-butyl-4-chloromethyl-2-(4-N-methyl-N-methyl-N-hexadecylsulfamoyl-2-nitrophenyl)-4-isoxazolin-3-one After mixing 550 g of 5-t-butyl-2-(4-N-methyl-N-hexadecylsulfamoyl-2-nitrophenyl)-4-isoxazolin-3-one prepared in the above step, 200 g of zinc chloride, 200 g of paraformaldehyde, and 1.5 liters of acetic acid, the mixture was refluxed for 10 hours while blowing hydrogen chloride gas into the reaction system. After the reaction was over, the reaction mixture obtained was cooled and poured into water. Crystals thus deposited were recovered by filtration and recrystallized from a 1:4 mixture of acetonitrile and methanol to provide 585 g of the above-described compound with a yield of 96%. The melting point thereof was 56° C.

| Elemental Analysis: | C (%) | H (%) | N (%) |
| --- | --- | --- | --- |
| Calcd. | 59.26 | 8.02 | 6.69 |
| Found | 59.20 | 8.13 | 6.78 |

EXAMPLE 5

Synthesis of Compound (10)

Synthesis Example 5-1

Synthesis of 5-t-butyl-2-(4-ethoxycarbonyl-2-nitrophenyl)-4-isoxazolin-3-one

In 100 ml of dimethyl sulfoxide were dissolved 23.0 g of ethyl of 4-chloro-3-nitrobenzoate and 17 g of 5-t-butyl-3-hydroxyisoxazole and after adding thereto 17 g of potassium carbonate, the reaction was performed for 8 hours at 75° C. After the reaction was over, the reaction mixture obtained was poured into cold diluted hydrochloric acid followed by stirring, whereby colorless crystals immediately deposited. The crystals were recovered by filtration and recrystallized from ethanol to provide 31.7 g of the above-described compound with a yield of 94.8%. The melting point thereof was 88° C.

Synthesis Example 5-2

Synthesis of Compound (10), 5-t-butyl-4-chloromethyl-2-(4-carboxy-2-nitrophenyl)-4-isoxazolin-3-one After mixing 260 g (0.778) of 5-t-butyl-2-(4-ethoxycarbonyl-2-nitrophenyl)-4-isoxazolin-3-one prepared in the above step, 700 ml of acetic acid, 27 g of zinc chloride, 105 g of paraformaldehyde, and 20 ml of sulfuric acid, the reaction system was saturated with hydrogen chloride gas at room temperature and the reaction was performed for 8 hours in a steam bath while further blowing hydrogen chloride gas into the system. Thereafter, 200 ml of water was added to the reaction system and the reaction was further performed for 5 hours. After the reaction was over, the reaction mixture was cooled and crystals thus deposited were recovered by filtration, washed with water, and dried to provide 234.5 g of the desired product with a yield of 85.0%. The melting point thereof was 217° C. (decompd.).

| Elemental Analysis: | C (%) | H (%) | N (%) |
|---|---|---|---|
| Calcd. | 50.79 | 4.26 | 7.90 |
| Found | 50.94 | 4.33 | 8.02 |

EXAMPLE 6

Synthesis of Compound (36), 5-t-butyl-4-chloromethyl-2-{4-(3-dodecyloxypropyl)-carbamoyl-2-nitrophenyl}-4-isoxazolin-3-one After mixing 130 g (0.366) of 5-t-butyl-4-chloromethyl-2-(4-carboxy-2-nitrophenyl)-4-isoxazolin-3-one (Compound (10) and 500 ml of chloroform, 52.3 g of thionyl chloride was slowly added thereto and the mixture was refluxed for 2 hours. After cooling the reaction mixture, the solvent and excessive thionyl chloride were distilled off under reduced pressure, and after adding 500 ml of chloroform to the residue, the mixture was cooled to 0° C. To the solution was added 63 ml of triethylamine and then 89 g of 3-dodecyloxypropylamine was gradually added dropwise to the mixture. Thereafter, the reaction was performed for one hour. After the reaction was over, the solvent was distilled off from the reaction mixture under reduced pressure and the residue was carefully applied to silica gel column chromatography to provide 110.4 g of the desired product as the main product with a yield of 52.0%. The product was an oily product.

| Elemental Analysis: | C (%) | H (%) | N (%) |
|---|---|---|---|
| Calcd. | 62.11 | 7.99 | 7.24 |
| Found | 62.04 | 8.05 | 7.19 |

EXAMPLE 7

Synthesis of Compound (2), 4-chloromethyl-5-t-butyl-2-(4-N-methyl-N-octadecyl-carbamoyl-2-nitrophenyl)-4-isoxazolin-3-one In 150 ml of dichloromethane was suspended 25 g (0.0705) of 5-t-butyl-4-chloromethyl-2-(4-carboxy-2-nitrophenyl)-4-isoxazolin-3-one (Compound (10)) and after adding 11.9 ml of triethylamine to the suspension, the mixture was cooled to 0° C. Then, 13.7 g of benzenesulfonyl chloride was slowly added dropwise to the mixture and the resultant mixture was stirred for 30 minutes. Then, 20 g of methyloctadecylamine was added thereto and the reaction was performed for 4 hours at 0° C. Thereafter, ethyl acetate was added to the reaction mixture and the organic phase formed was recovered and applied to silica gel column chromatography. The main product thus obtained was confirmed to be 4-chloromethyl-5-t-butyl-2-(4-N-methyl-N-octadecylcarbamoyl-2-nitrophenyl)-4-isoxazolin-3-one.

The product was recrystallized from methanol to provide 20.2 g (0.0326) of the desired product with a yield of 46.2%. The melting point thereof was 77° C.

EXAMPLE 8

Synthesis of Compound (11)

Synthesis Example 8-1

Synthesis of 5-methyl-2-(4-ethoxycarbonyl-2-nitrophenyl)-4-isoxazolin-3-one

After mixing 400 g of ethyl 4-chloro-3-nitrobenzoate, 1.2 liters of dimethyl sulfoxide, 270 g of 5-methyl-3-hydroxyisoxazole, and 292 g of potassium carbonate, the reaction was performed for 10 hours at 60° C. After the reaction was over, the reaction mixture was cooled and poured into water. Crystals thus deposited were recovered by filtration and recrystallized from ethyl acetate to provide 300.1 g of the above-described compound with a yield of 59.0%. The melting point thereof was 122° C. to 123° C.

Synthesis Example 8-2

Synthesis of Compound (11), 4-chloromethyl-5-methyl-2-(4-carboxy-2-nitrophenyl)-4-isoxazolin-3-one:

After mixing 279 g of 5-methyl-2-(4-ethoxycarbonyl-2-nitrophenyl)isoxazolin-3-one prepared in the above step, 700 ml of acetic acid, 129 g of paraformaldehyde, 156 g of zinc chloride, and 20 ml of sulfuric acid, the reaction system was saturated with hydrogen chloride gas at room temperature and the reaction was performed for 8 hours in a steam bath while further blowing hydrogen chloride gas into the system. Thereafter, 200 ml of water was added to the system and the reaction was further performed for 2 hours. After the reaction was over, the reaction mixture was cooled and then 2 liters of water was added thereto. Crystals thus deposited were recovered by filtration, washed with water, and dried to provide 199 g of the desired product with a yield of 66.7%. The melting point thereof was 190° C. to 191° C. (decompd.).

| Elemental Analysis: | C (%) | H (%) | N (%) |
|---|---|---|---|
| Calcd. | 46.10 | 2.90 | 7.81 |
| Found | 46.00 | 2.80 | 7.77 |

EXAMPLE 9

Synthesis of Compound (22), 4-chloromethyl-5-methyl-2-{4-(3-dodecyloxypropyl)-carbamoyl-2-nitrophenyl}-4-isoxazolin-3-one After mixing 130 g (0.432) of 4-chloromethyl-5-methyl-2-(4-carboxy-2-nitrophenyl)-4-isoxazolin-3-one (Compound (11)) 500 ml of acetonitrile, and 5 ml of dimethylformamide, 64 ml of thionyl chloride was slowly added to the mixture, and then the resultant mixture was refluxed for 2 hours. Thereafter, the solvent and excessive thionyl chloride were distilled off from the reaction mixture under reduced pressure and after adding 400 ml of chloroform to the residue formed, the mixture was cooled to 0° C. Then, 50.4 g of triethylamine was added to the mixture and after adding dropwise thereto 101 g of 3-dodecyloxypropylamine, the reaction was performed. After the reaction was over, the chloroform was distilled off from the reaction mixture and the residue was extracted with ethyl acetate and water. The extract formed was applied to a short column of silica gel and the product thus purified was recrystallized from a mixture of n-hexane and a small amount of ethyl acetate to provide 81 g (0.154) of the desired product with a yield of 35.6%. The melting point thereof 66° C. to 67° C.

| Elemental Analysis: | C (%) | H (%) | N (%) |
| --- | --- | --- | --- |
| Calcd. | 60.27 | 7.49 | 7.81 |
| Found | 60.51 | 7.59 | 7.75 |

EXAMPLE 10

Synthesis of Compound (20)

Synthesis Example 10-1

Synthesis of 5-t-butyl-2-(4-nitro-2-N-methyl-N-octadecylsulfamoylphenyl)-4-isoxazolin-3-one After mixing 62 g of N-methyl-N-octadecyl-2-chloro-5-nitrobenzenesulfonamide, 220 ml of diemthylformamide, 20.9 g of 5-t-butyl-3-hydroxyiosoxazole, and 20.7 g of potassium carbonate, the reaction was performed for 6 hours at 80° C. After the reaction was over, the reaction mixture was acidified with hydrochloric acid, the diemthylformamide was distilled off therefrom, and the residue was extracted with water and ethyl acetate. The organic phase thus obtained was applied to silica gel column chromatography to provide 29 g of the desired compound with a yield of 38.8%. The melting point thereof was 55° C. to 56° C.

Synthesis Example 10-2

Synthesis of Compound (20), 5-t-butyl-4-chloromethyl-2-(4-nitro-2-N-methyl-N-octadecylsulfamoylphenyl)-4-isoxazolin-3-one After mixing 20 g of 5-t-butyl-2-(4-nitro-2-N-methyl-N-octadecylsulfamoylphenyl)-4-isoxazolin-3-one prepared in the above step, 100 ml of acetic acid, 3 g of paraformaldehyde, and 5.4 g of zinc chloride, the mixture was refluxed for 7 hours while blowing hydrogen chloride gas into the reaction system. After the reaction was over, the solvent was distilled off from the reaction mixture under reduced pressure, the residue was dissolved in chloroform, and the solution was applied to silica gel column chromatography to provide 12.3 g of the desired product with a yield of 57.0%. The melting point thereof was 48° C. to 50° C.

| Elemental Analysis: | C (%) | H (%) | N (%) |
| --- | --- | --- | --- |
| Calcd. | 60.39 | 8.29 | 6.40 |
| Found | 60.26 | 8.30 | 6.30 |

EXAMPLE 11

Synthesis of Compound (23)

Synthesis Example 11-1

Synthesis of 5-methyl-2-(4-trifluoromethyl-2-nitrophenyl)-4-isoxazolin-3-one

After mixing 226 g of 4-chloro-3-nitrobenzotrifluoride, 129 g of 3-hydroxy-5-methylisoxazole, 336 g of sodium hydrogencarbonate, and 600 ml of dimethyl sulfoxide, the reaction was performed for 6 hours at 75° C. After the reaction was over, the reaction mixture obtained was poured into water, and crystals thus formed were purified by silica gel short column and recrystallized from a mixture of water and methanol to provide 176 g of the aforesaid compound with a yield of 61.1%. The melting point thereof was 122° C.

Synthesis Example 11-2

Synthesis of Compound (23), 4-chloromethyl-5-methyl-2-(4-trifluoromethyl-2-nitrophenyl)-4-isoxazolin-3-one After mixing 165 g (0.573) of 5-methyl-2-(4-trifluoromethyl-2-nitrophenyl)-4-isoxazolin-3-one prepared in the above step, 156.2 g of zinc chloride, 206.3 g of paraformaldehyde, and 5 ml of sulfuric acid, 400 ml of acetic acid was added to the mixture followed by stirring. The reaction system was saturated with hydrogen chloride gas at room temperature and the mixture was refluxed for 8 hours while blowing hydrogen chloride gas into the system. Thereafter, the reaction mixture was cooled and poured into ice-water and the product formed was extracted with ethyl acetate. Then, after removing colored components by a short column of silica gel, the product was recrystallized from a 4:1 mixture of n-hexane and ethyl acetate to provide 110 g of the desired product with a yield of 57%. The melting point thereof was 68° C. to 70° C.

| Elemental Analysis: | C (%) | H (%) | N (%) |
| --- | --- | --- | --- |
| Calcd. | 42.81 | 2.40 | 2.38 |
| Found | 42.51 | 2.30 | 2.16 |

EXAMPLE 12

Synthesis of Compound (33)

Synthesis Example 12-1

Synthesis of 5-phenyl-(4-ethoxycarbonyl-2-nitrophenyl)-4-isoxazolin-3-one

After mixing 200 g of ethyl 4-chloro-3-nitrobenzoate, 500 ml of dimethyl sulfoxide, 169 g of 5-phenylisoxazole, and 146 g of potassium carbonate, the reaction was performed for 5 hours at 60° C. After the reaction was over, the reaction mixture was cooled and poured into water. Crystals thus deposited were recovered by filtration, washed with water, and dried to provide 292 g of the above-described compound with a yield of 94.6%. The melting point thereof was 142° C. to 143° C.

Synthesis Example 12-2

Synthesis of Compound (33), 4-chloromethyl-5-phenyl-2-(4-ethoxycarbonyl-2-nitrophenyl)-4-isoxazolin-3-one After mixing 270 g (0.762) of 5-phenyl-(4-ethoxycarbonyl-2-nitrophenyl)-4-isoxazolin-3-one prepared in the above step, 800 ml of 1,2-dichloroethane, 125 g of zinc chloride, 103 g of paraformaldehyde, and 20 ml of sulfuric acid, the reaction was performed for 1.5 hours in a steam bath while blowing hydrogen chloride gas in the reaction system. During the reaction, crystals deposited. After cooling, water was added to the reaction mixture and crystals formed were recovered by filtration, washed with water, and dried to provide 270 g of the desired product with a yield of 88%. The melting point thereof was 190° C. to 191° C.

| Elemental Analysis: | C (%) | H (%) | N (%) |
|---|---|---|---|
| Calcd. | 56.66 | 3.75 | 6.95 |
| Found | 56.59 | 3.80 | 6.99 |

EXAMPLE 13

Synthesis of Compound (35)

Synthesis Example 13-1

Synthesis of 4-chloromethyl-5-phenyl-2-(4-carboxy-2-nitrophenyl)-4-isoxazolin-3-one After adding 300 ml of concentrated sulfuric acid to a mixture of 270 g (0.67) of 4-chloromethyl-5-phenyl-2-(4-ethoxycarbonyl-2-nitrophenyl)-4-isoxazolin-3-one (Compound (33)) and 2.5 liters of 1,4-dioxane, the resultant mixture was refluxed for 8 hours. Thereafter, the reaction mixture obtained was cooled and poured into water. Crystals thus deposited were recovered by filtration, washed with water, and dried to provide 210.2 g of the aforesaid compound with a yield of 83.7%. The melting point thereof was 186° C. to 189° C.

Synthesis Example 13-2

Synthesis of 4-chloromethyl-5-phenyl-2-{4-(3-dodecyloxypropylcarbamoyl)-2-nitrophenyl}-4-isoxazolin-3-one After adding 90.8 g of dicyclohexylcarbodiimide to a mixture of 150 g (0.400) of 4-chloromethyl-5-phenyl-2-(4-carboxy-2-nitrophenyl)-4-isoxazolin-3-one prepared in the above step and 600 ml of chloroform, the reaction was performed for 30 minutes at room temperature. Then, 97.4 g of 3-dodecyloxypropylamine was added dropwise to the reaction mixture and thereafter, the reaction was further performed for 5 hours. The reaction product was purified by a short column of silica gel and the product was recrystallized from acetonitrile to provide 78.0 g of the desired product with a yield of 33.4%. The melting point thereof was 110° C. to 111° C.

| Elemental Analysis: | C (%) | H (%) | N (%) |
|---|---|---|---|
| Calcd. | 64.04 | 7.05 | 7.00 |
| Found | 64.02 | 7.02 | 6.86 |

EXAMPLE 14

Synthesis of Compound (34)

Synthesis Example 14-1

Synthesis of 5-phenyl-2-(4-N-methyl-N-hexadecylsulfamoyl-2-nitrophenyl)-4-isoxazolin-3-one After mixing 300 g of N-methyl-N-hexadecyl-4-chloro-3-nitrobenzenesulfonamide, 122 g of 5-phenyl-3-hydroxyisoxazole, 800 g of dimethyl sulfoxide, and 106 g of potassium carbonate, the reaction was performed for 7 hours at 60° C. After the reaction was over, the reaction mixture obtained was cooled and poured into water. Crystals thus deposited were recovered by filtration, washed with water and then methanol, and dried to provide 376 g of the aforesaid compound with a yield of 99.3%. The melting point thereof was 88° C. to 89° C.

Synthesis Example 14-2

Synthesis of 4-chloromethyl-5-phenyl-2-(4-N-methyl-N-hexadecylsulfamoyl-2-nitrophenyl)-4-isoxazolin-3-one

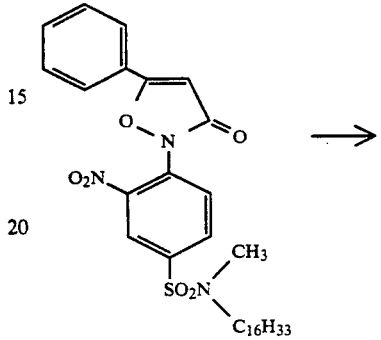

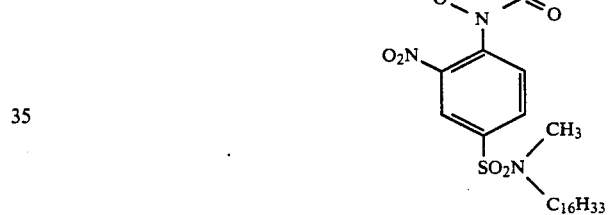

In 1.5 liters of ethylene chloride was dissolved 360 g of 5-phenyl-2-(4-N-methyl-N-hexadecylsulfamoyl-2-nitrophenyl)-4-isoxazolin-3-one and after adding thereto 98 g of zinc chloride and 81 g of paraformaldehyde, the reaction system was saturated with hydrogen chloride gas and then the mixture was refluxed for 3 hours while blowing hydrogen chloride gas into the reaction system. Thereafter, the reaction mixture was cooled, the solvent was distilled off, and the product was extracted with a mixture of ethyl acetate and water. The ethyl acetate was distilled off from the distrate, 2 liters of acetonitrile was added to the solids thus obtained, and the mixture was refluxed for 2 hours with stirring. The reaction mixture was cooled and crystals deposited were recovered by filtration to provide 339 g of the desired product with a yield of 87.2%. The melting point thereof was 95° C. to 97° C.

| Elemental Analysis: | C (%) | H (%) | N (%) |
|---|---|---|---|
| Calcd. | 61.14 | 7.15 | 6.48 |
| Found | 60.97 | 7.15 | 6.40 |

EXAMPLE 15

Synthesis of Compound (37)

Synthesis Example 15-1

Synthesis of 5-t-butyl-2-(4-methanesulfonyl-2-tetradecylsulfonylphenyl)-4-isoxazolin-3-one After mixing 32 g of 4-methanesulfonyl-2-tetradecylsulfonylchlorobenzene, 20 g of 5-t-butyl-3-hydroxyisoxazole, 20 g of potassium carbonate, and 140 ml of dimethyl sulfoxide, the reaction was performed for 4 hours at 80° C. After the reaction was over, the reaction mixture was poured into water and the product was extracted with ethyl acetate. The organic phase obtained was purified by silca gel column chromatography to provide 20.0 g of the aforesaid compound with a yield of 50.8%. The melting point thereof was 97° C. to 98° C.

Synthesis Example 15-2

Synthesis of Compound (37), 5-t-butyl-4-chloromethyl-2-(4-methanesulfonyl-2-tetradecylosulfonylphenyl)-4-isoxazolin-3-one After mixing 13 g of 5-t-butyl-2-(4-methanesulfonyl-2-tetradecylsulfonylphenyl)-4-isoxazolin-3-one prepared in the above step, 3.2 g of paraformaldehyde, 4.8 g of zinc chloride, 3 ml of sulfuric acid, and 100 ml of acetic acid, the mixture was refluxed for 7 hours while blowing hydrogen chloride gas into the reaction system. After cooling the reaction mixture, the mixture was poured into water and the product formed was extracted with ethyl acetate. The product obtained was purified by silica gel column chromatography to provide 11 g of the desired product with a yield of 77.7%. The melting point thereof was 110° C. to 111° C.

| Elemental Analysis: | C (%) | H (%) | N (%) |
|---|---|---|---|
| Calcd. | 73.47 | 7.65 | 2.95 |
| Found | 73.43 | 7.71 | 3.03 |

Examples of producing positive working compounds for silver halide photographic materials using the compounds of this invention are shown below as reference examples.

REFERENCE EXAMPLE

Reference Example 16-1

Synthesis of 4-(4-t-butoxycarbonylaminophenoxy)methyl-5-t-butyl-2-(4-N-methyl-N-octadecylcarbamoyl-2-nitrophenyl)-4-isoxazolin-3-one After mixing 10.0 g of 4-chloromethyl-5-t-butyl-2-(4-N-methyl-N-octadecylcarbamoyl-2-nitrophenyl)-4-isoxazolin-3-one prepared in Example 1, 4.0 g of 4-t-butoxycarbonylaminophenol, 3.0 g of potassium carbonate, and 100 ml of acetone, the mixture was refluxed for 7 hours.

After the reaction was over, the acetone was distilled off from the reaction mixture and the product formed was extracted with ethyl acetate and water. The organic phase thus obtained was purified by silica gel column chromatography to provide 9.0 g of the desired product with a yield of 70.5%.

Reference Example 16-2

Synthesis of 4-(4-aminophenoxy)methyl-5-t-butyl-2-(4-N-methyl-N-octadecylcarbamoyl-2-nitrophenyl)-4-isoxazolin-3-one In 100 ml of chloroform was dissolved 9.0 g of 4-(4-t-butoxycarbonylaminophenoxy)methyl-5-t-butyl-2-(4-N-methyl-N-octadecylcarbamoyl-2-nitrophenyl)-4-isoxazolin-3-one prepared in the above step and after cooling the solution below 5° C., 10 ml of trifluoroacetic acid was slowly added dropwise to the solution. Then, the mixture was allowed to gradually raise the temperature to room temperature and the reaction was performed for 10 hours. After the reaction was over, the reaction mixture obtained was poured in an aqueous sodium bicarbonate solution to neutralize it and extracted with ethyl acetate. The extract was purified by silica gel flash column chromatography to provide 6.9 g of the desired product with a yield of 90.8%.

Reference Example 16-3

Synthesis of Positive Working Compound A

In 40 ml of chloroform was dissolved 5.4 g of 4-(4-aminophenoxy)methyl-5-t-butyl-2-(4-N-methyl-N-octadecylcarbamoyl-2-nitrophenyl)-4-isoxazolin-3-one prepared in the above step and the solution obtained was cooled to 0° C. Then, 0.8 g of pyridine was added to the solution and after adding thereto 3.1 g of Compound A shown below, the mixture was reacted for 2 hours.

After the reaction was over, the chloroform was distilled off from the reaction mixture, the residue formed was dissolved in a small amount of dimethylformamide

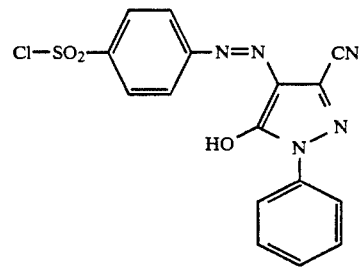

amide and after adding thereto methanol to an extent of not depositing oily matters, the mixture was stirred, whereby crystals deposited. The crystals were recovered by filtration and purified again by the same way as above to provide 3.9 g of Positive Working Compound A shown below with a yield of 46.5%. The melting point thereof was 157° C. to 159° C.

Positive Working Compound A:

-continued

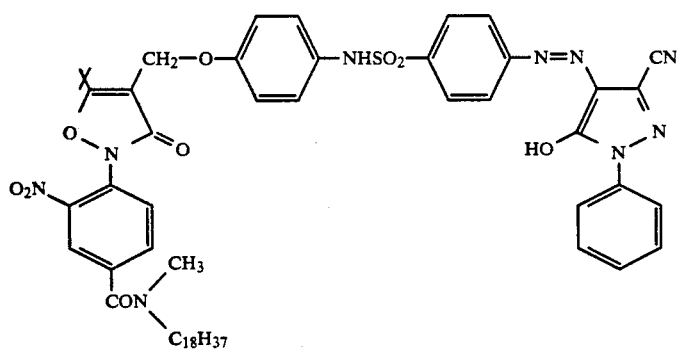

While the invention has been described in detail and with reference to specific embodiments thereof, it will be apparent to one skilled in the art that various changes and modifications can be made therein without departing from the spirit and scope thereof.

What is claimed is:

1. A compound of formula (I)

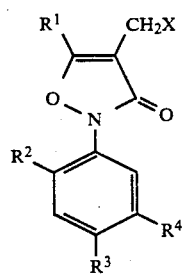

wherein $R^1$ represents an unsubstituted alkyl having 1 to 6 carbon atoms; an alkyl having 1 to 6 carbon atoms, which is substituted with chlorine, N-methylacetylamino, or octylthio; an aryl having from 6 to 24 carbon atoms, or an aryl having 6 to 24 carbon atoms which is substituted with methyl, chloromethyl, methoxy, hexadecyloxy, or sulfo; $R^2$, $R^3$ and $R^4$ represent hydrogen; an unsubstituted alkoxy having 1-16 carbon atoms; an alkoxy having 1-16 carbon atoms which is substituted with methoxy; an unsubstituted phenoxy; a phenoxy which is substituted with n-hexadecylcarbamoyl; an unsubstituted alkylcarbonyl having 1-12 carbon atoms; an unsubstituted phenylcarbonyl; a phenylcarbonyl which is substituted with ethoxycarbonyl; an unsubstituted alkoxycarbonyl having 1-17 carbon atoms; an unsubstituted phenoxycarbonyl; an unsubstituted carbamoyl; a carbamoyl which is substituted with an alkyl having from 1 to 18 carbon atoms, (2,4-di-t-pentylphenoxy)propyl, (3-hexadecylsulfamoyl)phenyl, or dodecyloxypropyl; an unsubstituted sulfamoyl; a sulfamoyl which is substituted with an alkyl having from 1 to 18 carbon atoms, phenyl, methoxypropyl, or methoxyethyl; an unsubstituted alkylsulfonyl having 1-14 carbon atoms; an alkylsulfonyl having 1-14 carbon atoms which is substituted with chlorine; an unsubstituted phenylsulfonyl; a phenylsulfonyl which is substituted with methyl; nitro; cyano; halogen; carboxyl; or trifluoromethyl; with the proviso that at least one of said $R^2$ and $R^3$ is cyano, an unsubstituted alkyl sulfonyl, an alkyl sulfonyl substituted with chlorine, an unsubstituted phenylsulfonyl, a phenylsulfonyl substituted with an alkyl, trifluoromethyl or nitro; and X represents fluorine, chlorine, bromine or iodine.

2. The compound as claimed in claim 1, wherein at least one of $R^2$ and $R^3$ is nitro.

3. The compound as claimed in claim 1, wherein $R^2$ and $R^3$ each is trifluoromethyl, cyano, an alkyl sulfonyl or an phenyl sulfonyl.

4. The compound as claimed in claim 2, wherein at least one of $R^2$, $R^3$, and $R^4$ is an alkyl sulfonyl, an phenyl sulfonyl, sulfamoyl, alkoxycarbonyl, carbamoyl, trifluoromethyl, or cyano.

5. The compound as claimed in claim 1, wherein $R^2$ is nitro, $R^3$ is sulfamoyl, carbamoyl, alkoxycarbonyl, or trifluoromethyl, and $R^4$ is hydrogen atom.

* * * * *